(12) United States Patent
Reintjes

(10) Patent No.: US 11,072,790 B2
(45) Date of Patent: Jul. 27, 2021

(54) DIRECTED EVOLUTION THROUGH MUTATION RATE MODULATION

(71) Applicant: Peter B. Reintjes, Durham, NC (US)

(72) Inventor: Peter B. Reintjes, Durham, NC (US)

(73) Assignee: Peter B. Reintjes, Durham, NC (US)

( * ) Notice: Subject to any disclaimer, the term of this patent is extended or adjusted under 35 U.S.C. 154(b) by 632 days.

(21) Appl. No.: 15/848,029

(22) Filed: Dec. 20, 2017

(65) Prior Publication Data

US 2018/0187182 A1 Jul. 5, 2018

Related U.S. Application Data

(60) Provisional application No. 62/437,034, filed on Dec. 20, 2016.

(51) Int. Cl.
| | |
|---|---|
| C12N 15/10 | (2006.01) |
| C07K 14/005 | (2006.01) |
| C12N 15/01 | (2006.01) |
| C12N 15/70 | (2006.01) |
| C40B 30/06 | (2006.01) |
| C40B 10/00 | (2006.01) |
| C12N 7/02 | (2006.01) |
| G01N 33/574 | (2006.01) |
| G01N 33/68 | (2006.01) |
| C12N 7/00 | (2006.01) |

(52) U.S. Cl.
CPC ........ *C12N 15/1058* (2013.01); *C07K 14/005* (2013.01); *C12N 7/00* (2013.01); *C12N 7/02* (2013.01); *C12N 15/01* (2013.01); *C12N 15/70* (2013.01); *C40B 10/00* (2013.01); *C40B 30/06* (2013.01); *G01N 33/574* (2013.01); *G01N 33/6893* (2013.01); *C12N 2795/14121* (2013.01); *C12N 2795/14151* (2013.01); *C12N 2795/14152* (2013.01); *C12N 2800/101* (2013.01)

(58) Field of Classification Search
CPC ................ C12N 7/00; C12N 15/01; C12N 2795/14121; C40B 10/00
See application file for complete search history.

(56) References Cited

U.S. PATENT DOCUMENTS

2018/0087046 A1* 3/2018 Badran ................ C12N 15/102

FOREIGN PATENT DOCUMENTS

| WO | WO 2010/028347 A2 * | 3/2010 | ............. C12N 15/10 |
| WO | WO 2012/088381 A2 * | 6/2012 | ............. C12N 15/09 |
| WO | 2012093128 A1 | 12/2012 | |
| WO | WO 2016/168631 A1 * | 10/2016 | ........... C07K 14/245 |

OTHER PUBLICATIONS

Joung et al., "Abacterial two-hybrid selection system for studying protein-DNA and protein-protein interactions" 97(13) Proceedings of the National Academy of Sciences USA 7382-7387 (Year: 2000).*
Diggle, et al., "Cooperation and conflict in quorum-sensing bacterial populations," Nature, 450, Nov. 15, 2007, pp. 411-414, doi:10.1038/nature06279, abstract.
Kunkel,et al., "Directed evolution to produce sludge communities with improved oxygen uptake abilities," Appl Microbiol biotechnol., 2015, pp. 1-10, doi:10.1007/s00253-015-6891-8.
Na D, et al., "Synthetic inter-species cooperation of host and virus for targeted genetic evolution," Journal of Biotechnology, 2011, vol. 153, pp. 35-41.
International Search Report and Written Opinion for PCT/US2017/067537, RU, dated May 4, 2018.

* cited by examiner

*Primary Examiner* — Nancy J Leith
(74) *Attorney, Agent, or Firm* — Daniel Cole; Olive Law Group, PLLC

(57) ABSTRACT

The present invention relates to methods and systems for the directed evolution of macromolecules. The methods involve increasing the mutation rate of an evolving organism comprising a gene of interest that encodes a gene product lacking a desired activity, whereby a mutated gene of interest is produced that encodes an evolved gene product comprising the desired activity and causing a suppression of mutagenesis. The systems comprise an evolving organism comprising a gene of interest encoding a gene product to be evolved, a host organism, and optionally, a lagoon, a cellstat and/or a suitable growth medium.

15 Claims, 5 Drawing Sheets

DIRECTED EVOLUTION THROUGH MUTATION RATE MODULATION

CROSS-REFERENCE TO RELATED APPLICATION

This application claims the benefit of U.S. Provisional Patent Application No. 62/437,034, filed Dec. 20, 2016, which is hereby incorporated herein in its entirety by reference.

FIELD OF THE INVENTION

The present invention relates to the field of directed evolution of nucleic acids and the gene products encoded thereby.

BACKGROUND OF THE INVENTION

Continuous evolution of bacteriophage has the potential to become a potent protein engineering tool. In this process, the continuous evolution of a microorganism rapidly produces a protein-encoding DNA sequence which has undergone many generations of mutation and selection for a particular property of said protein. The generality of this approach to protein engineering is limited by our ability to insert an expressible initial gene into the replicating microorganism and create a selection mechanism for the desired activity.

Currently the best practice in directed evolution exploits the rapid reproduction of M13 filamentous bacteriophage, a bacterial virus, to evolve novel proteins. A transformed *Escherichia coli* (*E. coli*) host cell provides a high level of mutation as well as a fitness selection mechanism that rewards virions exhibiting the desired property. As in natural evolution, directed evolution requires repeated cycles of the following three processes: (1) variation, or mutation, to allow for new or enhanced functionality; (2) selection that gives individuals with the desired new or enhanced functionality a reproductive advantage over individuals that exhibit a lesser degree of said functionality; and (3) reproduction to pass the selected functionality to the next generation.

Current continuous evolution procedures induce elevated mutation rates with external agents in order to rapidly sample a large portion of the evolutionary landscape. These elevated mutation rates must be avoided during the cultivation of host cells, and may be induced by an external agent when the host cells have been transferred to an environment where they are subject to infection by the evolving organism. As a result, both the replicating host cell and the virions being produced may contain a large number of mutations.

Engineering novel proteins via continuous evolution of bacteriophage currently requires the host bacteria to be transformed with two additional functions: (1) a mutagenesis vector that provides an elevated rate of viral mutation, and (2) a selection mechanism that gives a reproductive advantage to the genotype encoding the product producing the desired activity.

A technique known as Phage-Assisted Continuous Evolution (PACE) creates an environment for rapid evolution by inducing a high level of mutagenesis in the vessel containing the bacteriophage (U.S. Pat. No. 9,394,537). Because the mutagenesis is externally induced it affects all entities within this vessel. In particular, even uninfected *E. coli* cells experience an enhanced level of mutation as they grow and divide. The effects caused by the presence of *E. coli* mutants are mitigated by a carefully controlled flow rate which virtually ensures that a given *E. coli* cell spends less than one lifetime (division time) in the vessel containing the evolving bacteriophage. Flow rates between one and four volumes per hour can be sufficient to ensure that less than one percent of *E. coli* remain in the vessel long enough to divide and produce a daughter cell containing mutations.

Specifically, the PACE system requires: (1) A modified viral genome replacing a crucial phage gene with the gene to be evolved, (2) a transformed host with inducible mutagenesis, (3) a host plasmid containing a selection mechanism to provide the crucial phage gene in proportion to the desired activity of the evolving gene, and (4) an *E. coli* transit time close to the cell division time.

The PACE method removes a crucial gene from the M13 bacteriophage and substitutes the gene for the protein to be evolved, thus making the evolving protein a proxy for the protein required by the phage. The selection mechanism requires the host cell to produce, or withhold, this crucial phage protein to reward, or eliminate, the phage encoding the protein under consideration.

There are at least two aspects of this method that produce difficulties. First, removing the crucial gene from the phage produces a crippled phage that cannot be easily propagated prior to running the evolution experiment. Propagating the phage requires artificially providing the crucial protein. PACE includes an additional mechanism allowing external induction of the crucial protein's production.

The second difficulty involves the choice of the crucial phage gene employed by the current implementation of PACE: the fusion protein (pIII). The presence of this protein in *E. coli*, usually as the result of an infection by M13, evokes a response which prevents subsequent phage infection. This infection response is one of the reasons that *E. coli* infection by M13 is such an effective platform for directed evolution. The *E. coli* responds to and rewards the first M13 that infects it, and only produces phage progeny that are descendants of that phage. If super-infection were possible, the *E. coli* would produce progeny for multiple phage lineages with a selection mechanism subjected to the combined effects of their evolving proteins.

The mechanism by which the host produces the pIII fusion protein must not only be externally inducible, in order to propagate the crippled phage, but also held firmly in check until infection occurs. This is because the inadvertent production of pIII within the host cell evokes the infection response which prevents any phage infection.

Current directed evolution methods induce mutagenesis by introducing a mutagenic compound into the media of the vessel containing the evolving population of phage, thus conferring a global constant mutation rate on the population. This mutagenic compound could be a small molecule which directly causes mutation, or an inducer which triggers the production of error prone polymerase components. With this second method, cells producing different quantities of modified polymerase subunits will have corresponding DNA replication error rates. The ability to activate the expression of these mutagenic components within a host cell enables the present method.

SUMMARY OF THE INVENTION

The methods of the present invention implement a continuous evolution system that employs mutagenesis suppression as the selection mechanism. The desired activity of the evolving macromolecule results in a higher number of progeny identical to the parent, rewarding the genotype by increasing the number of phage carrying that genotype.

The methods of the present invention involve a host cell cultivation system supplying uninfected *E. coli* cells to a vessel containing a population of evolving bacteriophage. Said bacteriophage comprising a complete wild-type genome plus a gene for the protein to be evolved. As in other continuous evolution methods, mutagenesis is induced in the host cells, either globally or as a response to infection. The selection mechanism, however, consists of lowering the mutation rate in response to the desired activity of the evolving protein. Individuals containing DNA sequences encoding a protein with the desired activity will be rewarded with a lower mutation rate as they replicate, resulting in more progeny with a genotype identical to the parent phage. We refer to this selection method as Mutagenesis Selection, or M-Selection.

Phage encoding an evolving protein which does not exhibit the desired activity will continue to undergo the maximal induced mutation rate. While this selection mechanism does not immediately eliminate non-performing individuals, their lines of descent will experience extinction due to error catastrophe within a few generations. Unless, of course, one of the mutants expresses an improvement to the evolving protein, in which case its progeny will begin to experience a reduced mutation rate and therefore more faithful reproduction.

The methods of the present invention have the property that lines of descent with increased levels of the desired activity will search the evolutionary landscape less aggressively, while non-performing individuals continue to explore the mutation space aggressively, at the risk of their lines of descent experiencing error catastrophe.

In one embodiment of the invention, a method described herein further employs the *E. coli* infection response, the phage shock promoter, as one method of inducing the elevated mutagenesis. Thus, uninfected host cells are not subject to enhanced mutation and can remain in the lagoon indefinitely awaiting infection. Infected cells grow more slowly than uninfected cells as energy is devoted to phage production and this slows the cell life-cycle, reducing the requirement for a high flow rate. Furthermore, infected cells only produce pre-infected daughter cells eliminating any interaction between a mutated *E. coli* and subsequent generations of phage.

The present methods of mutagenesis selection reduce the difficulty of propagating a crippled phage. As in classical phage display, the protein to be evolved is added to a fully functional phage. Mutagenesis selection also avoids the problems associated with unwanted pIII production in the host cell by eliminating the need for a host plasmid to encode the pIII gene.

An important difference between PACE and the current disclosure is that mutagenesis is not externally induced, therefore, uninfected cells are not mutated allowing the production of a minimum number of faithful copies before the infected host expresses mutagenesis products. It may prove useful to retain the arabinose-induced mutagenesis of PACE as a way of achieving a moderate baseline mutation rate in the lagoon.

This lack of externally induced mutagenesis and therefore mutagenesis in uninfected cells eases the restriction to a lagoon transit time of one host cell lifecycle. Furthermore, M13 infection slows the doubling time of *E. coli*, further relaxing this constraint. If uninfected cells propagate in the lagoon, they will not be mutated and if infected cells propagate, the daughter cells will be pre-infected and simply continue to shed the virus infecting the parent with the mutation level established by the original infection. Thus, a broader range of flow rates can be used in mutagenesis selection.

Another important difference between the methods of the present invention and PACE is the less aggressive search of the mutation space as the desired activity improves. Genotypes experiencing elevated activity search the mutation space less aggressively while mutants with little or no activity continue to aggressively search the mutation space. This use of a mixed population and weak selection delays fixation of genotypes, allows extended access to the evolutionary landscape, and helps insure that the system does not get trapped at a local fitness peak.

Because no critical genes are removed from the phage, it can be easily propagated prior to beginning the process of directed evolution. The problems associated with the presence of pIII in the host and the associated premature infection response are avoided since no phage genes are incorporated into a host plasmid. An additional negative selection mechanism can be added either by blocking the repressor molecule or separately expressing additional mutagenic components.

DETAILED DESCRIPTION OF THE INVENTION

Figure 1:
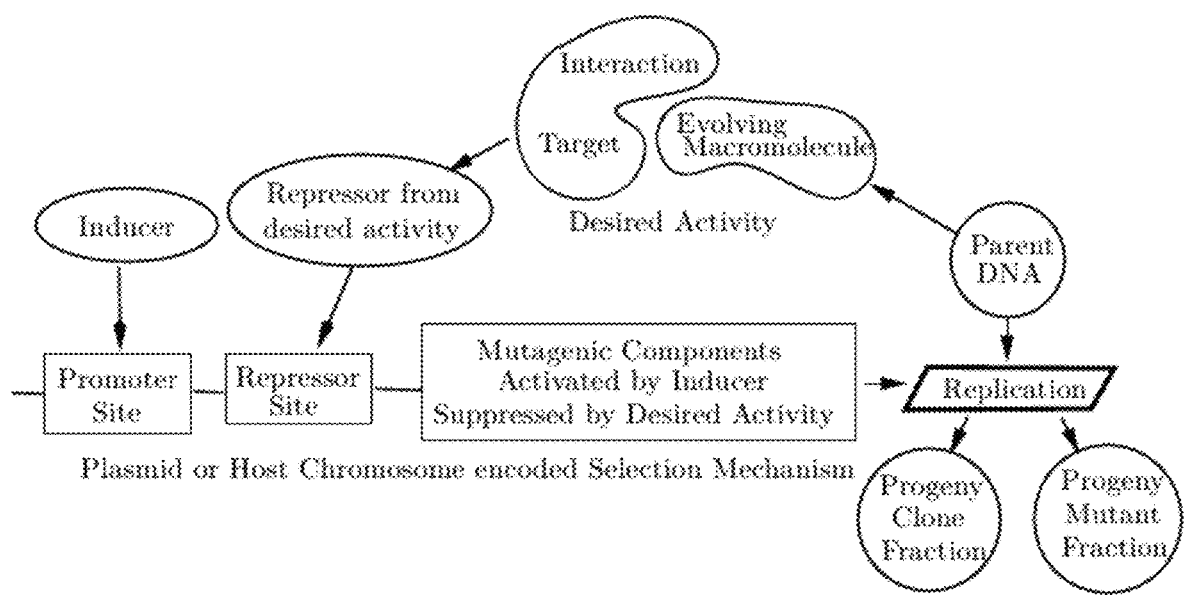
FIG. 1 shows a general schematic of Mutagenesis Selection (M-Selection)

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Definitions

A "desired activity" is the property of the evolving gene product (e.g. a protein or RNA) that we wish to enhance. For example, the desired activity can be the ability to bind with another protein or to a specific nucleotide sequence in a nucleic acid molecule (e.g. dsDNA, ssDNA, ssRNA, dsRNA, and the like) which is designated as the target. The desired activity can also be an enzymatic activity. It is recognized that the initial minimal level or amount of the desired activity can be further enhanced using the methods of the present invention. For example, the desired activity can be binding of the evolving gene product to a particular protein. Initially, the desired activity can be a minimum level of binding of the gene product to the particular protein sufficient to cause a minimal suppression of mutagenesis. However, using the methods of the present invention, the level of binding of the gene product to the particular protein can be further increased or enhanced whereby the suppression of mutagenesis is further enhanced.

A "target" is the protein or nucleic acid substrate we are seeking to affect. The target is produced by the host organism and not subjected to evolutionary pressure. For example, this could be the protein or nucleic acid substrate, particularly a specific nucleotide sequence therein, to which we want our evolving protein to bind.

A "host organism" is a microorganism that is transformed with one or more nucleic acid molecules, whereby the transformed microorganism is capable of affecting the reproduction of the evolving organism based upon a desired activity exhibited by the evolving or evolved gene product. Preferably, the microorganism should not be subject to evolutionary pressure.

A "selection mechanism" is the process by which a particular desired activity results in increased reproduction of the entity encoding the genes associated with that activity. For example, a protein carried by a phage subjected to elevated mutation rate is selected based on how well it binds to a second protein not subjected to evolutionary pressure.

A "cellstat" is a vessel in which the host cells are propagated prior to infection by the evolving organism (e.g. bacteriophage). The cellstat environment is designed to maintain low levels of mutagenesis and avoid selective pressure on the host cells (e.g. bacterial cells, *E. coli* cells).

A "lagoon" is the vessel in which the population of host organisms (e.g. bacteria) come into contact with and can be infected by the population of evolving organisms (e.g. bacteriophage) and where the subsequent generations of evolving organism are maintained. The lagoon environment is designed to enhance mutagenesis in order to accelerate evolution of the gene of interest and the gene product encoded thereby.

"Error catastrophe" is extinction caused by accumulation of excessive mutations.

"Weak selection" is the inability of an organism to become fixed in an evolving population because its fitness is only slightly elevated above the fitness of its competitors.

By "population" is intended to mean two or more individuals but typically, a population of the present invention will comprise $10^4$, $10^5$, $10^6$, or more individuals (e.g. bacteriophage, bacteria) it is recognized that the number of individuals in a population of the present invention can vary depending on any number of factors including, for example, the volume of the lagoon or other vessel, the species of evolving organism, the species of host organism, and the environmental conditions.

A "evolving organism" is the organism comprising the gene of interest encoding the gene product of interest to be evolved. A preferred evolving organism of the present invention is a virus, particularly bacteriophage, more particularly M13.

"Super-infection" is the infection of a single host cell with more than one virus.

Description

Extremely high, yet controllable, in vivo mutation rates are now possible. This broad-spectrum mutagenesis, with as much as $10^5$ times the basal mutation rate, can be controlled within an individual host cell. If this mutagenesis is initiated by infection, say with the phage shock promoter, but then reduced by the desired activity the two principal components of evolution will be satisfied. The increased number of identical phage progeny produced by individuals exhibiting the desired activity will select for the desired activity. This is mutagenesis selection. While previous methods induce a uniform mutagenesis in the lagoon, mutagenesis selection induces a unique level of mutagenesis within each infected host cell.

Although Clones versus Mutants may sound like the title of a bad science fiction movie, it precisely states how Mutagenesis Selection operates. The process creates more mutants if the genotype does not encode a protein with the desired property, and more clones if the genotype leads to the expression of a protein with the desired property. The level of mutagenesis is modulated between maximum mutagenesis in the presence of proteins exhibiting none of the desired activity and a very low level of mutagenesis when proteins that exhibit the desired activity are produced.

It is necessary to produce two clones per generation that infect hosts to produce enough phage to prevent washout of a genotype. Assuming phage production of 100/hour and a lagoon transit time of one hour, a maximum mutation rate of four (4) mutations per genome will avoid washout. The percentage of phage progeny which are exact copies of the parent is given by the Poisson distribution where $\mu=0$ is the expected number of mutations and $\lambda$ is the mutation rate per virion (mutation rate/base*6.4 kbp/genome). A mutation rate of $\lambda=4$ gives a 1.8% probability of zero mutations.

$$P(\mu, \lambda) = \frac{e^{-\lambda}\lambda^\mu}{\mu!} \rightarrow P(0, 4) = \frac{e^{-4}}{1} = .018$$

So the maximum per-base mutation rate that a genome could tolerate and have any clones remain in the lagoon is $4/6400=6.25\times10^{-4}$. The basal rate of *E. coli* producing M13 phage is $7.2\times10^{-7}$. Taking a phage production average of 100/hour for normal M13 infection, and assuming a one hour transit time for the host cell, would require a minimum cloning rate of 2%: two faithful copies per infection in order to avoid washout. The previous consideration of high mutation rates would seem to allow slower flow rates, which will lower this minimum fraction.

FIG. 1 shows a general outline of the Mutagenic Selection process. An inducer activates mutagenesis by enabling expression of the mutagenic components. When the desired activity occurs, a repressor protein is expressed and suppresses the expression of said mutagenic components. The amount of mutagenesis suppression is proportional to the amount of desired activity. The reduction in mutagenesis increases the number of phage progeny that have no mutations.

Figure 2:
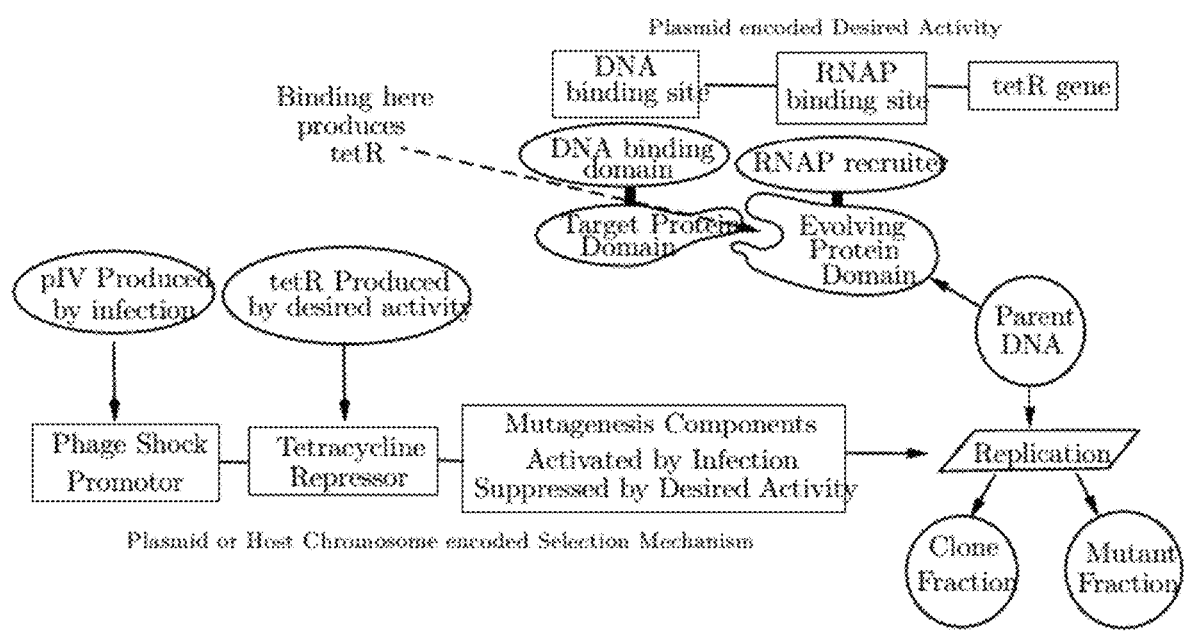
FIG. 2 shows an exemplar of M-Selection using phage shock promoter and Tet repressor wherein two-hybrid protein-protein binding causes expression of the tetracycline repressor gene (tetR) to produce the tetracycline repressor protein (TetR) which can bind to a tetracycline response element or other tetracycline operator sequence in the plasmid or modified host chromosome to block transcription from the phage shock promoter.

FIG. 2 shows one example of how this might work. Interaction between a target protein, expressed constitutively by the host organism and not subject to evolutionary pressure, and the evolving protein, encoded by the phage and expressed in the host after infection, causes the expression of a repressor which reduces the expression of the mutagenic components. Increases in the binding affinity between the target and the evolving protein results in greater levels of expression of the repressor and therefore lower mutation rates within that host cell. The phage shock promoter is an exceptionally good inducer to activate the nominal level of mutation, ensuring that only infected cells will have higher levels of mutation. Because the phage-shock promoter is activated by the p4 protein (pIV) expressed after infection, and the repressor is activated by the expression of the evolving protein, the activator and repressor components will be simultaneously competing to modulate the mutation rate.

Figure 3:
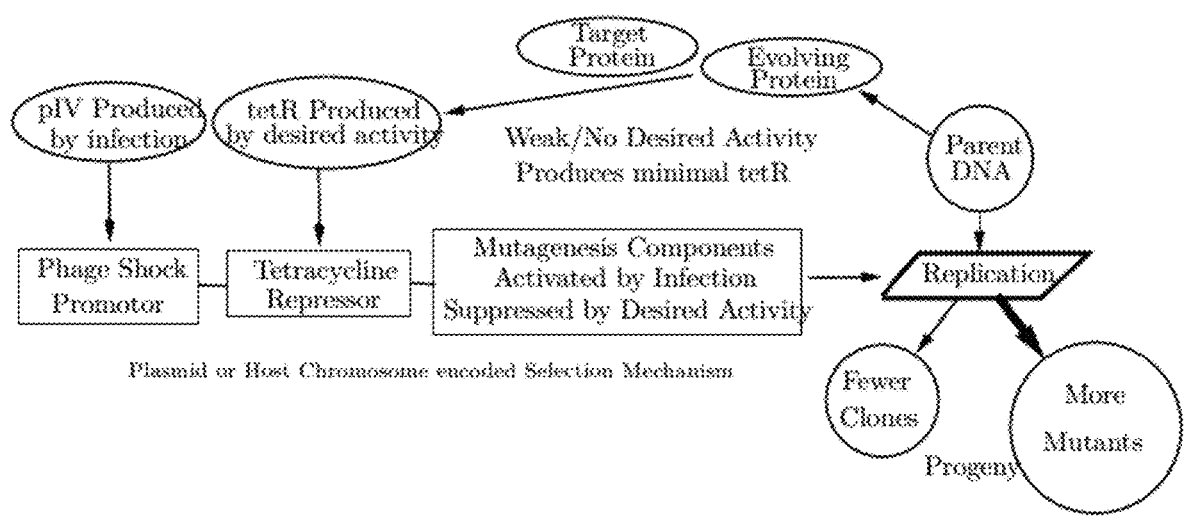
FIG. 3. shows an exemplar responding to a phage exhibiting a low level of the desired activity. Weak binding allows for a higher rate of mutation.

FIG. 3 shows the exemplar responding to a phage which encodes an evolving protein which has a low level of the desired behavior, in this case, binding with the target protein. Because little or none of the repressor is expressed, the mutation rate remains at the high level established by the reaction to the phage shock promoter. The progeny produced by the host organism will contain a large number of mutants, thus aggressively searching the evolutionary landscape, and few clones, or exact copies, of this non-performing phage genotype will be produced.

Figure 4:
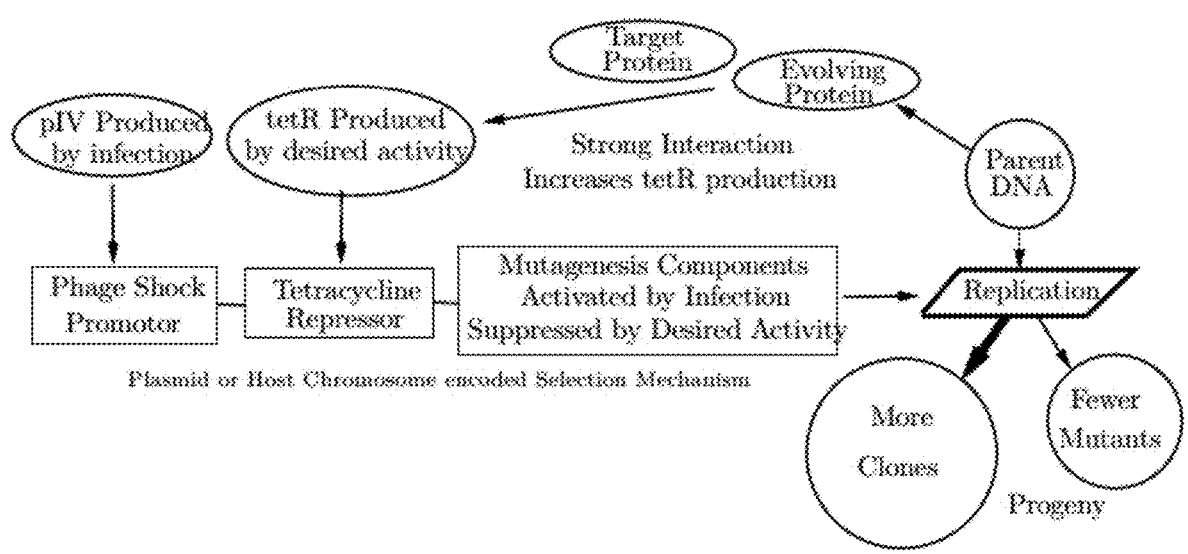
FIG. 4. shows an exemplar responding to a phage exhibiting a high level of the desired activity. Strong binding produces more clones.
Figure 5:
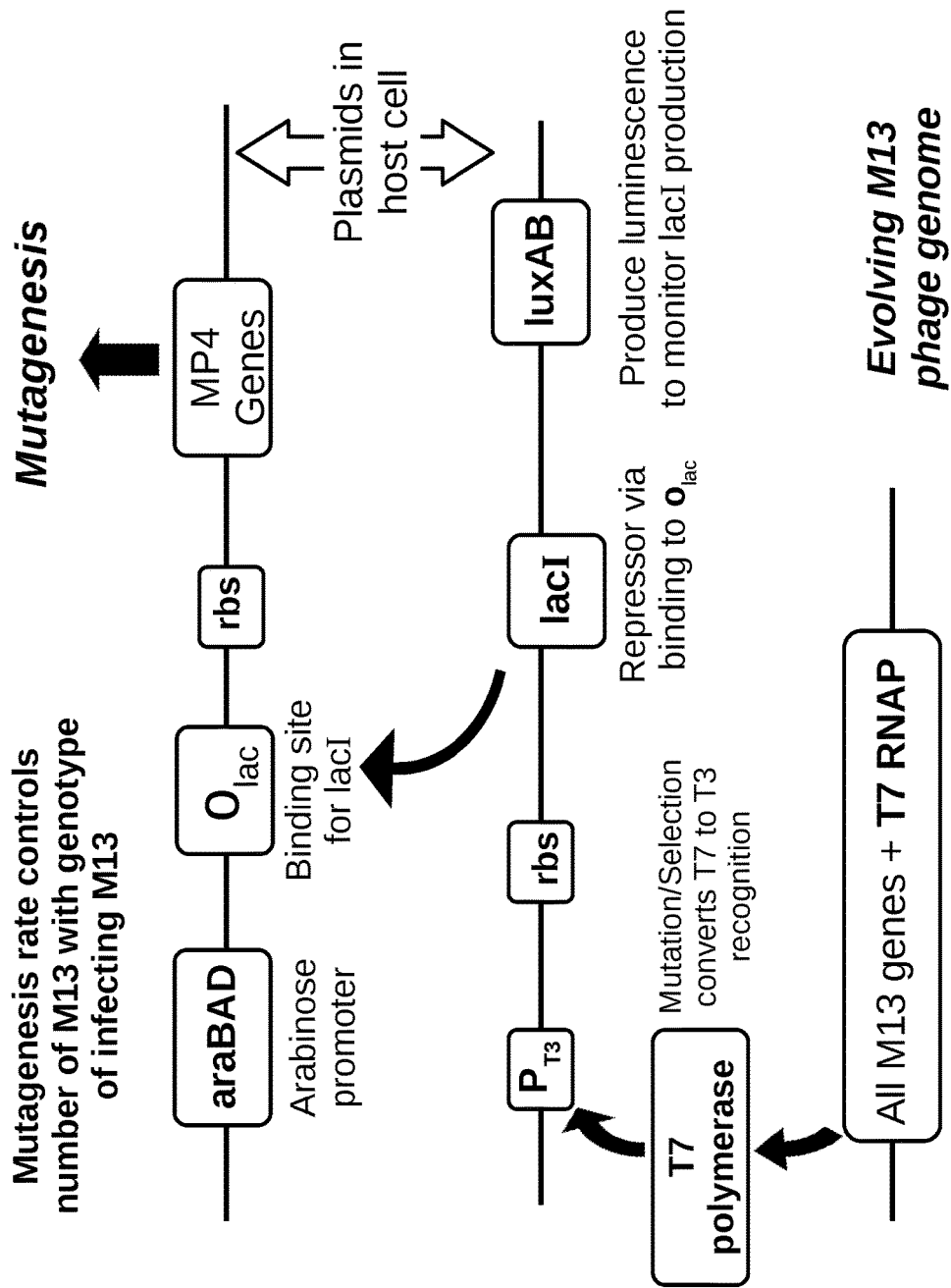
FIG. 5 shows an exemplar of M-selection to evolve T7 polymerase to recognize or bind T3 polymerase promoter.

FIG. 4 shows the exemplar responding to a phage encoding a protein which has a high level of the desired activity. The strong binding between the evolving protein and the target results in enhanced expression of the repressor, resulting in lower production of the mutagenic components, and therefore a lower mutation rate. Fewer of the resulting progeny will contain mutations, resulting in a less aggressive search for variation, and more of the progeny will carry exact copies of this genotype encoding the protein with the high level of desired activity.

Non-limiting embodiments of the invention include, for example, the following embodiments.

1. A method of directed evolution of macromolecules, the method comprising increasing artificially the mutation rate experienced by a population of an evolving organism comprising a gene of interest to be evolved, wherein the gene of interest encodes a gene product that does not comprise a desired activity, whereby the gene of interest evolves in one or more of the evolving organisms so as to encode an evolved gene product comprising the desired activity, wherein the mutation rate decreases proportionally in response to the production of the evolved gene product comprising the desired activity, whereby the one or more evolving organisms comprising the evolved gene of interest are favored for reproduction in the population and at decreased mutation rate.

2. The method of embodiment 1, wherein the evolving organism requires a host organism to replicate.

3. The method of embodiment 2, wherein the host organism is engineered for an increased mutation rate, relative to the mutation rate of a host organism that is not engineered for an increased mutation rate.

4. The method of embodiment 2 or 3, wherein increasing artificially the mutation rate experienced by the population of the evolving organism comprises contacting the population of the evolving organism with a population of the host organism, wherein optionally the contacting occurs in a lagoon.

5. The method of embodiment 4, wherein the engineered host organism comprises a plasmid or a modified host chromosome containing a set of inducible genes encoding one or more mutagenic components.

6. The method of embodiment 5, wherein the one or more mutagenic components are selected from the group consisting of a modified DNA polymerase protein domain that is capable of reducing the fidelity of DNA replication by a DNA polymerase in the host organism and a protein that is capable of interacting with a DNA polymerase in the host organism so as to reduce the fidelity of DNA replication by the DNA polymerase.

7. The method of any one of embodiments 1-5, wherein increasing the mutation rate comprises introducing a plasmid containing a phage shock promotor that is capable of inducing the production of the mutagenic components.

8. The method of any one of embodiments 1-6, wherein the mutation rate is decreased by a repressor molecule that is produced proportionally to the production of the desired activity and down regulates expression of the mutagenic components.

9. The method of embodiment 7, wherein in the mutation rate is decreased by a repressor molecule that is produced proportionally to the production of the desired activity and down regulates expression of the mutagenic components.

10. The method of embodiment 8 or 9, wherein the repressor is the tetracycline repressor (TetR) and the plasmid comprises a binding site for TetR, the binding site comprising a tetracycline response element or one or more repeats of the tetracycline operator sequence.

11. The method of any one of embodiments 1-10, wherein mutagenesis is increased by the introduction of a mutagenic compound to the environment of the evolving organism.

12. The method of embodiment 1, wherein the evolving organism is a modified M13 bacteriophage, and wherein the genome of said evolving organism comprises a subset of the wild-type M13 phage genes comprising gIII, gIV, and the DNA sequences of the origin of replication and the packaging signal, wherein all other M13 phage genes necessary for phage propagation are encoded in a plasmid contained in a host organism and expressed either constitutively, as a response to phage infection, or through inducement by an external agent.

13. The method of any one of embodiments 2-11, wherein the evolving organism is a modified M13 bacteriophage, and wherein the genome of said evolving organism comprises a subset of the wild-type M13 phage genes comprising gIII, gIV, and the DNA sequences of the origin of replication and the packaging signal, wherein all other M13 phage genes necessary for phage propagation are encoded in the plasmid in the host organism and expressed either constitutively, as a response to phage infection, or through inducement by an external agent.

14. The method of any one of embodiments 2-13, wherein the evolving organism is a bacteriophage and the host organism is a bacterium.

15. The method of any one of embodiments 2-14, wherein the host organism is *Escherichia coli* (*E. coli*).

16. A system for the directed evolution of macromolecules, the system comprising:
(a) a population of an evolving organism comprising a gene of interest to be evolved, wherein the gene of interest encodes a gene product that does not comprise a desired activity, whereby the gene of interest is capable of evolving in one or more of the evolving organisms so as to encode an evolved gene product comprising the desired activity and the capability to suppress directly or indirectly induced mutagenesis, and wherein the evolving organism requires a host organism to replicate; and (b) a population of the host organism, wherein the host organism is engineered for an increased mutation rate, relative to the mutation rate of a host organism that is not engineered for an increased mutation rate.

17. The system of embodiment 16, further comprising at least one member selected from the group consisting of a vessel, a cellstat, and a growth medium suitable for propagation of the evolving organism and/or host organism.

18. The system of embodiment 16 or 17, wherein the evolving organism is a bacteriophage and the host organism is a bacterium.

19. The system of embodiment 18, wherein the bacteriophage is M13 and the host organism is E. coli.

20. The system of embodiment 19, wherein the M13 bacteriophage is a modified M13 bacteriophage comprising a subset of the wild-type M13 phage genes comprising gIII, gIV, and the DNA sequences of the origin of replication and the packaging signal, wherein all other M13 phage genes necessary for phage propagation are encoded in a plasmid contained in the host organism and expressed either constitutively, as a response to phage infection, or through inducement by an external agent.

21. The system of embodiment 16 or 17, wherein the evolving organism is the evolving organism of any one of embodiments 1-15.

22. The system of any one of embodiments 16, 17, and 21, wherein the host organism is the host organism of any one of embodiments 2-15.

Alternative Embodiments

Other mechanisms can be employed to lower the mutation rate in response to the desired activity, including but not limited to RNA interference with the mRNA encoding the mutagenic polymerase components, stimulating the production of high-accuracy polymerase components, or the activation of anti-mutator genes.

As new methods to induce high mutation rates are developed, they will undoubtedly suggest new methods to modulate the resulting rates of mutation. It will thus be an obvious extension of this method to employ that modulation as a selection mechanism in continuous evolution.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means "40% or less than 40%. When, in this specification, a range is given as "(a first number) to (a second number)" or "(a first number)–(a second number)," this means a range whose limits include both numbers. For example, "25 to 100" means a range whose lower limit is 25 and upper limit is 100, and includes both 25 and 100.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of directed evolution of DNA encoded macromolecules, the method comprising increasing artificially the mutation rate experienced by a population of evolving organisms comprising a gene of interest to be evolved, wherein the gene of interest encodes a gene product that does not comprise a desired activity, whereby the gene of interest evolves in one or more of the evolving organisms within the population of evolving organisms so as to encode an evolved gene product comprising the desired activity, wherein the mutation rate decreases proportionally in response to the production of the evolved gene product comprising the desired activity, whereby the one or more evolving organisms comprising the evolved gene product comprising the desired activity are favored for reproduction in the population of evolving organisms and at decreased imitation rate when compared to the one or more evolving organisms without the evolved gene product comprising the desired activity.

2. The method of claim 1, wherein the evolving organisms require a host organism to replicate.

3. The method of claim 2, wherein the host organism is engineered for an increased mutation rate, relative to the mutation rate of a host organism that is not engineered for an increased mutation rate.

4. The method of claim 3, wherein increasing artificially the mutation rate experienced by the population of the evolving organisms comprises contacting the population of the evolving organisms with a population of the host organism, wherein optionally the contacting occurs in a lagoon.

5. The method of claim 4, wherein the engineered host organism comprises a plasmid or a modified host chromosome containing a set of inducible genes encoding one or more mutagenic components.

6. The method of claim 5, wherein the one or more mutagenic components are selected from the group consisting of a modified DNA polymerase protein domain that is capable of reducing the fidelity of DNA replication by a DNA polymerase in the host organism and a protein that is capable of interacting with a DNA polymerase in the host organism so as to reduce the fidelity of DNA replication by the DNA polymerase.

7. The method of claim 5, wherein increasing the mutation rate comprises introducing a plasmid containing a phage shock promoter that induces the production of the mutagenic components.

8. The method of claim 7, wherein the mutation rate is decreased by a repressor molecule that is produced proportionally to the production of the desired activity and down regulates expression of the mutagenic components.

9. The method of claim 8, wherein the repressor is a tetracycline repressor (TetR) and the plasmid comprises a binding site for TetR, the binding site comprising a tetracycline response element or one or more repeats of a tetracycline operator sequence.

10. The method of claim 5, wherein the mutation rate is decreased by a repressor molecule that is produced proportionally to the production of the desired activity and down regulates expression of the mutagenic components.

11. The method of claim 5, wherein the one or more evolving organisms modified M13 bacteriophages, and wherein the genome of said one or more evolving organisms comprises a subset of wildtype M13 phage genes comprising gIII, gIV, and the DNA sequences of the origin of replication and the packaging signal, wherein all other M13 phage genes necessary for phage propagation are encoded in the plasmid in the host organism and expressed either constitutively, as a response to phage infection, or through inducement by an external agent.

12. The method of claim 11, wherein the host organism is *E. coli*.

13. The method of claim 1, wherein mutagenesis is increased by the introduction of a mutagenic compound to the environment of the population of evolving organisms.

14. The method of claim 1, wherein the one or more evolving organisms are modified M13 bacteriophages, and wherein the genome of said one or more evolving organisms comprises a subset of wild-type M13 phage genes comprising gIII, gIV, and the DNA sequences of the origin of replication and the packaging signal, wherein all other M13 phage genes necessary for phage propagation are encoded in a plasmid contained in a host organism and expressed either constitutively, as a response to phage infection, or through inducement by an external agent.

15. The method of claim 14, wherein the host organism is *Escherichia coli* (*E. coli*).

* * * * *